United States Patent [19]

Anderson

[11] Patent Number: 5,244,799
[45] Date of Patent: Sep. 14, 1993

[54] PREPARATION OF A POLYMERIC HYDROGEL CONTAINING MICROPORES AND MACROPORES FOR USE AS A CELL CULTURE SUBSTRATE

[76] Inventor: David M. Anderson, 337 Squire Hall Suny, Buffalo, N.Y. 14114

[21] Appl. No.: 809,259

[22] Filed: Dec. 17, 1991

Related U.S. Application Data

[63] Continuation of Ser. No. 574,506, Aug. 23, 1990, abandoned, which is a continuation of Ser. No. 323,616, Mar. 14, 1989, abandoned, which is a continuation-in-part of Ser. No. 292,615, Dec. 30, 1988, abandoned, which is a continuation-in-part of Ser. No. 52,713, May 20, 1987, abandoned.

[51] Int. Cl.$^5$ .................. C12N 5/00; C12N 11/08; C08F 20/10; C08G 69/08
[52] U.S. Cl. .................. 435/240.23; 424/487; 435/174; 435/180; 523/106; 525/937; 526/328; 528/310
[58] Field of Search ............... 435/174, 177, 180, 182, 435/240.23; 424/484, 487; 523/105, 106, 113; 525/937; 521/50, 64, 65; 526/328; 528/310; 204/194, 403

[56] References Cited

U.S. PATENT DOCUMENTS 3,860,490  1/1975  Guttag .................. 435/182
4,519,909  5/1985  Castro .................. 210/500.2

FOREIGN PATENT DOCUMENTS 0060138  9/1982  European Pat. Off. .

Primary Examiner—David M. Naff
Attorney, Agent, or Firm—Blodgett & Blodgett

[57] ABSTRACT

A hydrophilic substituent of a bicontinuous cubic phase in equilibrium is polymerized and the unpolyermized components subsequently removed and replaced with water, creating a hydrogel which is locally highly cross-linked but of high water content because of the presence of a periodic network of water-filled macropores superposed on the hydrogel matrix. The diameter of these "macropores" can be preselected between 20 Angstroms and several hundred Angstroms or even higher, and in general will be much larger than the "micropores" within the hydrogel portions of the final material. The material has high water content, good mechanical integrity and notch strength, high permeability to oxygen, and the pore size can be chosen to allow passage of molecules of pre-selected size. The material is useful as a cell culture substrate and in a contact lens and other biological and medical applications.

7 Claims, No Drawings

PREPARATION OF A POLYMERIC HYDROGEL CONTAINING MICROPORES AND MACROPORES FOR USE AS A CELL CULTURE SUBSTRATE

REFERENCE TO RELATED APPLICATIONS

This application is a continuation of application Ser. No. 07/574,506, filed Aug. 23, 1990, which is a continuation of application Ser. No. 07/323,616, filed Mar. 14, 1989which is a continuation-in-part of application Ser. No. 07/292,615, filed Dec. 30, 1988, which is a continuation-in-part of application Ser. No. 07/052,713, filed May 20, 1987, all now abandoned; the disclosures of which are hereby incorporated by reference.

FIELD OF THE INVENTION

The invention pertains to hydrogel applications, particularly soft contact lenses, but also other medical/biological applications where high strength at high water content, biocompatibility, and/or macroporosity are necessary or desirable.

BACKGROUND OF THE INVENTION

It is well known that the optimal hydrophilic contact lens should have as high water content as possible, yet have good mechanical integrity and notch strength. High water content lessens the irritation of the eye, establishes a high degree of hydrophilicity which leads to better lubrication during blinking, and most importantly, it is known that the permeability of oxygen through the lens increases exponentially with water content. Furthermore, the lens should have a large effective pore size so as to allow the passage of not only low-molecular weight tear film components, such as metabolites (glucose, urea, lactic acid, etc.) and ions, but also higher-MW components such as proteins and mucins, thus minimizing the effect of the lens on the distribution of these components in the preocular tear film (POTF) without the need for tear exchange under the lens. In prior art contact lenses these have represented conflicting requirements and compromises have had to be made. For example, good integrity requires a high degree of cross-linking and thus low water content and small effective porsize. Lenses such as Sauflon 70, which are made from copolymers of hydrophilic and relatively hydrophobic monomers, have a high water content, but the tear film over these lenses has been found to be definitely thinner and less stable than the normal POTF (note that some authors use the term pre-corneal tear film, or PCTF, instead of POTF), whereas the pre-lens tear film (PLTF) over lenses made from PHEMA, a very hydrophilic polymer, were found to be very similar to the normal POTF. Furthermore, the use of PVP (polyvinylpyrrolidone) to achieve high water content results in lenses which yellow with age.

The desired properties have been obtained, and the difficulties of prior materials have been overcome in a novel and unobvious manner by the present invention. Other properties and advantages will become apparent in what follows.

SUMMARY OF THE INVENTION

In the present invention, a hydrophilic substituent of a bicontinuous cubic phase is polymerized according to the methods disclosed in the copending applications cited above, and the unpolymerized components subsequently removed and replaced with water, thus creating a hydrogel which is locally highly cross-linked but nevertheless of high water content because of the presence of a periodic network of water-filled pores superposed on the hydrogel matrix. We will use the word "macropores" to refer to this periodic network of water-filled pores resulting from the cubic phase microstructure. The diameter of these macropores can be preselected, by methods taught in the applications cited above, to be between 20 Angstroms and several hundred Angstroms or even higher, and in general will be much larger than the "micropores" within the hydrogel portions of the final material. A simpler way to understand this superstructure is to imagine taking an ordinary hydrogel, with say, 10 Angstroms average diameter micropores and "drilling" a network of pores of, say, 100 Angstroms diameter and filling these macropores with water. By adjusting the composition of the cubic phase, the volume fraction $phi_g$ of the hydrophilic substituent—usually a hydrophilic monomer such as 2-hydroxyethyl methacrylate (HEMA) with added cross-linker and usually swollen with added water—can be made considerably less than 50%. If $phi_m$ is the volume fraction of monomer in the hydrophilic constituent then the volume fraction of water in the final macroporous hydrogel will be $1 - phi_g + phi_g(1 - phi_m)$; that is, the water content in the final material has two contributions, one from the water in the hydrogel portion of the microstructure, and one from the much larger macropores. For example, for the cubic phase with didodecyl-dimethylammonium bromide (DDAB) as the surfactant, $phi_g$ can be chosen between 11% and 70%, so that if $phi_m$ is 60%, then the final water content can be chosen between 58 and 93%.

DETAILED DESCRIPTION OF THE INVENTION AND PREFERRED EMBODIMENTS

Effect of macropores on physical properties

A fundamental advantage of this material is that the strength of the final material can be made much higher than a simple hydrogel at the same water content. This is because the shear modulus $G_s$ of a simple hydrogel is a very strong nonlinear function of the water content, whereas the same shear modulus of a macroporous material depends only linearly on the macroporosity. In a simple gel at equilibrium swelling, if $v_1$ is the molar volume of the solvent, and X is the interaction parameter between the solvent and the polymer, then the shear modulus is $$G_s = RT[\ln(1 - phi_m) + phi_m + X phi_m^2]/[v_1(phi_m^{\frac{1}{3}} - phi_m)]$$

Thus, for example, the shear modulus of poly-cis-1,4-butadiene decreases from $1.35 \times 10^7$ dynes/cm$^2$ to $2.56 \times 10^5$ dynes/cm$^2$ when the water content increases from 56% to 82%, a decrease in strength of fifty-fold. On the other hand, the shear modulus of a macroporous material depends only linearly on its porosity. Thus if the water content in the same rubber were increased from 56 to 82% by the "drilling" of macropores of 26% volume fraction, then the decrease in shear modulus would be expected to be on the order of only 30%, instead of a factor of fifty. The reason for the dramatic decrease in strength in the first case is of course due to the much lower concentration of cross-links in the simple gel, in addition to the higher water concentration.

An analogy can be drawn with structural parts in, for example, airplanes where high strength and low weight are required. It is common engineering practice to use high-strength materials in which large holes are removed to decrease weight, with only a modest decrease in strength. This thus represents a higher strength-to-weight ratio than, for example, a thinner piece of the same material but without holes. In the present invention, the macropores which are analogous to these holes are formed by the additional step of forming a bicontinuous cubic phase in which one of the continuous components is an aqueous solution of hydrophilic monomer, which is polymerized in the same way as in the formation of a simple hydrogel. Thus the chemistry of the final hydrogel is the same as in the simple hydrogel, after the removal of the unpolymerized surfactant (and possibly hydrophobic component), and the only difference is the presence of the macropores.

As mentioned above, the oxygen (and carbon dioxide) permeability depends exponentially on the water content of the lens. At 25° C., the oxygen diffusion rate for a wide variety of hydrogels, in units of cc(STP).mm/cm$^2$.sec.cm Hg, is given by:

$$P_d = 1.5 \times 10^{-9} \exp(4.09 phi_w)$$

Thus for example, an increase from 70% water (as in Sauflons 79) to 90% increases oxygen permeability by 126%. This has lead to great efforts on the part of contact lens manufacturers to develop hydrogels of very high water content. The macropores of the present invention represent a sensible and effective means of arriving at high water contents without sacrificing mechanical integrity. Furthermore, another impetus for increasing the water content is the fact that dry contact lenses cause abrasion to the cornea. Contact lenses made from silicon-based rubbers, for example, have high oxygen permeability, but are the cause of considerable discomfort due to their hydrophobicity, and collect mucous and lipid deposits, eventually leading to contraction and crazing.

The role of higher-MW tear film components passed by macropores.

In addition to the higher water content at the same or greater strength, the macropores provide for transport of higher-molecular weight tear components throughout the eye-lens system. Many of the essential functions of the POTF (or the PLTF)—optical, metabolic, lubricant, and antimicrobial—depend on the distribution of these higher-MW components. The outermost layer of the lacrimal film is essential to a high quality refractive surface. This layer is also important in preventing tear evaporation and lowering surface tension. The lubricating and wetting roles of the POTF are necessary in blinking which in turn is necessary for cleaning the epithelial surface. And as in other mucousal surfaces, the POTF plays an important role in protecting the epithelial surface from microbial attack and other toxins, and provides a compatible environment for the epithelium. The precise characteristics of the epithelial cells, in turn, change the light transmission characteristics; when the refractive index of the intercellular spaces become lower than that of the intracellular medium, glare and haloes result, and transparency can be reduced. The action of the lids during blinking is known to be sufficient to render the surface of a contact lens wettable by the tear film by the spreading of its surface active mucus components, but the pre-lens tear film formed on contact lenses is noted for its decreased stability in comparison to the corresponding preocular tear film. This decreases as reflected in a quicker break up time, is due to the structural differences between the two tear films, as their different mucus, aqueous and lipid components vary in conformation and thickness. These facts point to the possibility of an extremely important role for the macropores of the present invention in reducing the effect of the lens on the composition and functioning of the tear film.

Proteins cannot in general pass through prior art soft contact lenses because of the small effective pore sizes. In one study over 80% of subjects wearing contact lenses (42 PHEMA lenses, 6 PMMA, and 2 silicone-based) had abnormal tear protein profiles. Neither can mucins pass through prior art hydrophilic lenses. The most prevalent mucins have molecular weights of approximately 400,000. The mucus layer of the eye protects the underlying epithelial surface from microorganisms, the toxins they produce, and other antigens. Mucins are highly tensioactive (Holly and Hong 1982) and appear to be crucial in maintaining the wettability of the eye or the contact lens; the mucins serve as a bridge between the hydrophobic epithelial surface of the cornea and the aqueous salt layer of the tear film. Thus without the mucin layer, the tear fluid would not wet the epithelium and would "bead up". Enzymes that are found in the normal POTF include lysozyme, peroxidase, amylase, B-hexosaminidase, arylamidase, arylsulphatase, acid and alkaline phosphatase, plasminogen activator, angiotensin converting enzyme, and lactate dehydrogenase, the pore size in the present materials are in the correct range and monodispersity to allow for selection of the proteinaceous and macromolecular components which are to pass through the material.

In order to permit the spread of the tear film over the eye quickly after blinking, the tensions at the surface of the lens should be low. By choosing the macropores of the present invention so as to allow a homogeneous distribution of the necessary lipids and mucins throughout the eye-lens system, these surface tensions should be much closer to the tensions found at the cornea-tear film interface in the normal (lens-free) eye. This should minimize the occurrence of dry patches. In addition to the well-known detrimental effects on the eye caused by dry patches, a further complication promoted by a short tear break-up time (or BUT) is the occurrence of gelatinous deposits in the soft contact lens itself. Besides causing irritation of the eye, such spoilation of the lens can lower oxygen transmission through the lens leading to other complications such as epithelial edema, erosion or necrosis, stromal edema, superficial or deep corneal vascularization, enhancement of endothelial dysfunction, and inflammatory reactions.

In addition to surface tension, another important physical property of the tear film, which is affected by components that can pass through macropores but not micropores, is viscosity. It is known that the higher-MW components of the tear film render the film shear-thinning. This is necessary to maintain the film when the eye is open, but to enhance lubrication, through shear-thinning, during blinking.

The macropores of the present invention could also be of importance in passing the bacteriacidal components of the tear film, which include lysozyme (muramidase), B-lysine, lactoferrin, and a-arysulphatase, and lacrimal immunoglobulins. For example, abnormally low concentrations of lysozyme in the tear film lead to keratoconjunctivitis sicca.

Other relatively high MW compounds that may reach the corneal epithelium through the tear film, and whose passage could be selectively controlled in the present invention by the presence of macropores of selected size, include nutritional components, such as Vitamin A, and topically-administered drugs. It has been shown that Vitamin A, a deficiency of which results in keratinizing, as well as retinoids can be therapeutic when administered topically to the eye. Thus the lenses of the present invention could be particularly beneficial in cases where corrective lenses are used in conjunction with such treatments.

Other applications.

Hydrogels are used in many other applications besides contact lenses, and the high strength at high water content, biocompatibility, and macroporosity of the present invention could make these materials of great potential importance in many of these, in particular in skin applications such as soft tissue substitutes, burn dressings, suture coatings, and drug-delivery patches. In these skin applications the possibilities opened up by the ability of the macropores to act in a similar role as the pores of normal skin are obvious. As cell culture substrates, the ability to select the macropore size could be important, both for controlling the passage of nutrients to the cell and the nature of the cell sites themselves. For use as intraocular lenses, artificial corneas, vitreous humor replacements, and eye capillary drains, the discussions herein concerning contact lenses point to obvious advantages of the present materials. Other medical applications of hydrogels include catheters, artificial larynges, urethral prostheses, and in plastic surgery.

In an embodiment as described in application Ser. No. 07/292,615, preparation of the hydrogel began with a mixture of 1 gm of the surfactant didodecyldimethylammonium bromide (DDAB) (registry number 3282-73-3), 1.4 ml of distilled water, and 0.26 ml of methylmethacylate (MMA) which had been purified by vacuum distillation and to which had been added 0.004 gm/ml of azobisisobutyronitrile (AIBN). The mixture was stirred vigorously with a magnetic stir bar in a capped vial (when styrene was used instead of MMA, stirring had to be very gentle). After a few minutes magnetic stirring became impossible because of high viscosity, which together with optical isotropy as checked by observation between crossed polarizing lenses indicate a cubic or 'viscous isotropic' phase. At approximately the same volume fractions but with alkanes such as decane or dodecane, cubic phases have been verified in both cases by Small angle X-ray Scattering. After equilibrating for a week at 23 C., the mixture was smeared onto the end of the plunger of a large syringe, and pushed through an 18 gauge needle into a 1.5 mm i.d. x-ray capillary. After loading and sealing of the capillary, the sample remained clear and optically isotropic. The optical isotropy of cubic phases is due to the equivalence of the three principle directions; other liquid crystalline phases are birefringent.

The capillary was then placed in a photochemical reactor having four UV lights, emitting radiation at 350 nm. The sample was exposed for 36 hours, to bring about radical chain polymerization of the MMA via the decomposition of AIBN into initiating radicals. By the end of this time the sample was opaque white in appearance.

In application Ser. No. 07/292,615 an experiment was described in which a clear, polymerized cubic phase was produced by the UV polymerization of the aqueous acrylamide (plus cross-linker) component of a DDAB/decane/water+acrylamide+cross linker+initiator bicontinuous cubic phase. The weight fraction corresponding to the aqueous phase was 65%. X-ray then verified that the polymerized structure still possessed cubic symmetry. We now describe the removal of the unpolymerized components of a similar specimen to create water-filled macropores.

The nonionic surfactant $C_8E_4$, with a hydrocarbon tail of 8 carbons and a polar end consisting of 4 ethylene oxide groups, forms normal micelles in water to over 30% concentration at room temperature. The applicant has determined that, although DDAB alone does not form normal micelles in water, it is capable of forming mixed micelles, apparently, with $C_8E_4$. Thus, 5% DDAB was added to a 15% solution of $C_8E_4$ in water, and the $C_8E_4$/water micellar solution remained a clear, isotropic, low viscosity, single-phase solution. Then 5% decane was added, and again the solution remained a clear, isotropic, low viscosity, single-phase solution. This meant that the unpolymerized components, DDAB and decane, could be removed by the incorporation of these components into $C_8E_4$/DDAB/decane swollen, normal micelles. Specifically, this was done by placing the specimen in water and very slowly dripping in a 25% aqueous solution of $C_8E_4$, such that a final concentration of $C_8E_4$ of 15% was reached in approximately two days. The amount of water and $C_8E_4$ used to remove the DDAB and decane in the specimen was large enough that the concentrations of DDAB and decane in the final solution were very small, considerably lower than 5%. The specimen was then removed from this solution, except of course for the small volume of solution remaining in the macropores of the specimen, which was replaced with water by successive dilutions.

The removal of DDAB was established by titration of the drawn-off solution with silver nitrate. Silver nitrate is water soluble whereas silver bromide forms a colored precipitate, which turns deep red on exposure to light. Silver nitrate was thus added to the drawn-off solution, and ion exchange occurred with the DDAB counterions yielding silver bromide, which precipitated. After a few minutes exposure to sunlight, the precipitate turned a deep red. We did not attempt to weight the precipitate to check that all of the DDAB in the specimen was present in the solution. However, we did the following qualitative check. The amount of DDAB in the specimen was calculated and this amount dissolved in $C_8E_4$ and water, as above. Then silver nitrate was added, and the precipitate observed to change color as just described. The amount of precipitate was checked visually to be comparable to the amount formed from the solution in question. In view of the simplicity of the removal/dilution procedure, it is effective as a means to remove the unpolymerized components to form water-filled macropores.

This removal of DDAB and decane (as well as the water-soluble initiator) was performed very slowly in order to minimize, or avoid, disruptive effects on the periodic miscrostructure. Indeed, the final result was a perfectly clear, isotropic specimen, which was a rubbery solid. Clearly the preferred experiment to prove that this last step did not disrupt the periodic structure, would have been x-ray. Unfortunately, the electron density contrast between the macropores and the PAM gel matrix is extremely low (after all, the gel itself is 85% water), so that good x-ray diffractograms are not possible without somehow enhancing the contrast. One attempt was made to enhance contrast, namely by placing the specimen in a very concentrated solution of a protein, in hopes that the protein would be small enough to enter the macropores, but not the micropores in the PAM gel matrix. The protein which has been tried so far is cytochrome-c, which definitely penetrated into the macropores as evidenced by a strongly red-colored specimen after sitting overnight in a 40% aqueous solution. However, the diffractogram was not of good quality. There are a number of possible reasons for the poor diffractogram. One reason is that the entire periodic order was destroyed. This is extremely unlikely, however, since there was no visual change in the sample, the sample should become cloudy (actually milky in all probability) if the periodicity was entirely destroyed. Another possibility is that the cytochrome-c was able to penetrate into the micropores as well as the macropores. This is quite possible because the MW of cyochrome is small enough that it could probably enter the micropores at the present concentrations. Presently we are at work to repeat the x-ray experiment with a different protein and with a longer specimen-film distance (which means much longer run time). However, since the periodic ordering survived the polymerization procedure, evidence indicates that it also survived the removal/dilution step, particularly in view of the optical clarity of the final product.

As mentioned above, the final material was the consistency of rubber, and can be cut into thin slices each having good elastic properties. Because the volume fraction of the gel portion is 65%, and 15% of this gel is (cross-linked) polyacrylamide, the overall volume fraction of polymer is less than 10%, meaning that the water content is over 90%. This can be adjusted over a very large range. In particular, we have found that with styrene as the oil, the cubic phase region extends from about 70% water down to approximately 11% water, and the same range appears to hold with toluene as oil. When 15% acrylamide (plus cross-linker) is added to the water component, this range shrinks somewhat at the low water end but is still very large in extent; at 20% AM in the water the cubic phase is somewhat harder to locate, and at 30% harder still. Near 65% water the addition of AM has less effect than at the lower water contents, which means that it should be possible to repeat the process described above near 65% aqueous phase but with 20%, 30%, or perhaps even higher percentage of AM in the aqueous phase. This would bring the water contents down to 80% or so. Since we have found cubic phases at approximately 50% water with 15% AM in the aqueous phase, we can reach water contents of 92.5%, for example.

Polyacrylamide is one typical representative of a class of related hydrophilic polymers, and although the phase behavior will probably change slightly when another monomer such as HEMA is used instead, the cubic phase region will still be present in this DDA system. Furthermore, the following are examples of parameters which can be changed so as to counteract changes in the phase behaviour that might reduce the size of the cubic phase region: 1) the length of the hydrocarbon tails of the surfactant can be increased or decreased; 2) the counterion can be exchanged for chloride, fluoride, etc; 3) the temperature can be adjusted; 4) the oil can be changed (note that the effect of changing from decane to styrene is to extend the lower limit of the cubic phase region from about 30% down to 11%); 5) the head group area can be adjusted by substituting other moieties for the methyl groups, for example (this has been done in the case of DOPC and has induced a cubic phase; 6) a co-surfactant, such as an alcohol, can be added.

Clear polymerized cubic phase using cetyltrimethylammonium chloride

A clear specimen of polymerized bicontinuous cubic phase has been produced which, after the removal of the surfactant, is 92.8% water. The surfactant used was the single-tailed cationic surfactant cetyltrimethylammonium chloride, or CTAC. CTAC, as well as other closely related surfactants including CTAS (sulfur as counterion), CTAB (bromide), CTAF (fluoride), and DoTAC (dodecyltrimethylammonium chloride), forms a bicontinuous cubic phase near 80% surfactant in water at temperatures generally 40° C. or higher. The particular structure of these cubic phases is predicted to be the Ia3d structure (space group #230), from x-ray experiments. This is the same space group that is found for the cubic phases in many biological lipid/water systems (such as monoolein/water), but in the case of CTAC and related surfactants the cubic phase is normal rather than reversed—that is, the two rod networks are filled with surfactant tails rather than water, and the water forms the continuous matrix which is bisected by the "gyroid" minimal surface. Thus the cubic phase is found between the normal hexagonal and the lamellar phases. This means that the appropriate component to polymerize is the aqueous component, and then removal of the surfactant creates two interwoven but disconnected macropore networks.

It is important to distinguish this cubic phase from the other cubic phase in the same system at much lower surfactant concentration. This latter cubic phase occurs near 50% surfactant in the CTAC, CTAS, and DoTAC systems, and extends to lower temperatures. The space group is Pm3n, and at this time there is considerable debate in the community as to whether the structure is bicontinuous or not. The present applicant favors a model—which is not bicontinuous because it is best in accord with the NMR self-diffusion and relaxation studies performed at the University of Lund in Sweden.

The water component of the cubic phase at higher surfactant concentrations in the CTAC/water system was replaced by a 30 wt. % aqueous solution of acrylamide. The concentration of CTAC was 75.9% by weight. In addition to acrylamide, the crosslinking agent methylene-bis-acrylamide was added along with the water-soluble initiator 4 4'-azobis-(4-cyanovaleric acid) (ACVA). The components were sealed in a glass tube and the tube centrifuged back and forth in order to mix the components. The sample was then put in an oven at 42° C. for two weeks to equilibrate. It is probably an important point that the atmosphere above the sample in the tube was air and not nitrogen, because the oxygen in the sample then acted to inhibit any polymerization of the acrylamide. After two weeks of equilibration, the test tube was broken open, and the air above the sample was replaced with nitrogen gas and the tube then sealed with a cork. This was then placed in a photochemical reactor with 3500 Angstrom lamps. The temperature was maintained at 40° C. during the polymerization, which was carried out for 3 days.

At the end of this time the sample was clear with a slightly bluish tint. After the sample was removed from the test tube, it had become opaque white. However, when placed in water it became clear again, beginning at the outer surface and working in toward the center, so that after about two hours it was entirely clear. During this time it was obvious visually that the surfactant was being removed from the sample and replaced by water, one could see a stream of the surfactant coming from the sample and rising to the top of the water, in the same manner that the surfactant is observed to appear in pure water without mechanical mixing.

The specimen at the end of this procedure was clear with a slight bluish tint, isotropic through crossed-polarizers, with a gravimetric density slightly greater than water. All of these facts indicate a cubic macropore structure superimposed upon a 30% PAM hydrogel, although as in the DDAB case it is difficult to establish the cubic symmetry with x-ray due to the low electron density contrast. In terms of mechanical properties, the specimen is about 0.3 grams in weight and hangs together as a single contiguous piece, which is remarkable since it is only 7.2% polymer. The consistency is rubbery as in the DDAB case, and the shape is maintained even after the sample is gently deformed.

Two other potential systems which could yield negative-charged porewells.

Several additional cubic phases have been chosen for polymerization experiments, cubic phases which are based on anionic surfactants: sodium dodecyl sulphate (SDS) and sodium n-dodecanoate. Based on earlier work, we have formed a cubic phase with composition: 20% SDS, 0.8% butanol, 42% water, and 37.2% stryene. Then with the surfactant sodium n-decanoate, have shown that two cubic phases exist with this surfactant, one in the binary surfactant/water system above 67° C., and one in the ternary surfactant/water/toluene (or decane) system at about 20% toluene, at 60° C. The former cubic phase is almost certainly bicontinuous since it lies between a hexagonal and a lamellar phase region. The latter cubic phase has not been fully characterized, although the water concentration and toluene content are very similar (50% and 20% respectively) to those in the bicontinuous DDAB cubic phase, thus suggesting bicontinuity. Furthermore, the fact that toluene can be incorporated into the latter cubic phase by raising the temperature to 60° C. suggests that it can also be added to the former cubic phase by raising the temperature above 67° C. In addition, isotropic signals observed in $^2$H NMR experiments on the nearby lamellar phase have been interpreted as possibly indicating a cubic phase at 67° C. in the ternary system. With these facts in mind, and by taking advantage of the parameters listed above which allow for further control of phase behavior, evidence indicates that a bicontinuous cubic phase can be produced from sodium n-decanoate, or a related surfactant, and significant amounts of styrene, which behaves nearly identically to toluene.

In particular, a surfactant can be used which is similar to SDS, or to sodium n-decanoate, but has a polymerizable group in the tail, preferably a methacrylate group. The styrene would then be polymerized together with the surfactant. This is a preferred method for two reasons: 1) the electrostatic profile of the styrene molecule is such that it will not tend to penetrate into the head group region of the surfactant layer, so that the styrene/methacrylate end group region should be a contiguous region rather than uninterrupted by the presence of hydrocarbon tails or surfactant polar groups, making for good polymerization conditions; and 2) the porewalls of the resulting polymerized phase will be anionic, thus reducing or eliminating any tendency for absorption of tear components to the surface.

Specifically, the aromatic ring of the styrene molecule can be roughly described as a "sandwich", with a middle layer of positive net charge surrounded by two layers of negative net charge. This provides for a very favorable styrene/head group interaction in the case of a cationic surfactant, in which the styrene molecule is sandwiched between two cationic groups. Thus, while the molecule will always tend to penetrate into the head group region of a cationic surfactant layer, this favorable interaction in the cationic case will not be available in the anionic surfactant layer. We have performed NMR experiments indicating that the styrene in the DDAB/styrene/water cubic phase is indeed located preferentially near the head group region. With SDS or sodium decanoate, the styrene should be located almost entirely in a separate layer starting near the end of the surfactant tails. If these surfactant tails contained a methacrylate group at their ends, this would create nearly ideal conditions for a polymerization which would polymerize both the styrene and the surfactant.

Such a polymerization would then result in a macroporous material with water already in the pores, thus eliminating the need for the removal of unpolymerized components. We expect that, as in the case of the acrylamide polymerizations described herein, the absence of obstructions such as hydrocarbon tails in the component undergoing polymerization will create a favorable medium for polymerization which will lead to clear polymeric materials. Furthermore, negatively charged porewalls are optimal in terms of reducing or eliminating absorption of proteinaceous material to the material. By using mixtures of polymerizable and normal surfactants, one could then control very precisely the charge on the porewalls so as to optimize it for the application.

The creation of controlled-charge porewalls with the resulting properties is advantageous not only for the applications newly disclosed in the present application but also for many of the embodiments disclosed in the applications which are incorporated herein by reference. This subject matter is considered a further aspect of the present invention.

Clearly, minor changes may be made in the form and construction of this invention and in the embodiments of the process without departing from the material spirit of either. Therefore, it is not desired to confine the invention to the exact forms shown herein and described but it is desired to include all subject matter that properly comes within the scope claimed.

The invention having been thus described, what is claimed as new and desired to secure by Letters Patent is:

1. A process of making a stabilized polymeric hydrogel material having a matrix containing macropores and a fixed, highly connected network of water-filled macropores, comprising the steps of:
   (a) forming a mixture of a hydrophilic monomer, polymerizing agent, an ionic surfactant, and water;
   (b) mixing said mixture until it forms a viscous isotropic phase;
   (c) equilibrating said phase for at least one week until it forms a cubic phase;
   (d) causing said hydrophilic monomer to polymerize in the cubic phase to form a cubic phased body;

(e) locating said body in a water bath;
(e) adding to said water bath a noniomic surfactant which holds the ionic surfactant in the water bath and thereby causes the ionic surfactant to diffuse out of the body; and
(f) separating said body from said water bath to obtain said hydrogel material.

2. A process as recited in claim 1, wherein said ionic surfactant is selected from the group consisting of didodecylammonium halide, cetyltrimethyl ammonium halide, cetyltrimethyl ammonium sulfide, didecly-trimethyl ammonium chloride, sodium dodecylsulphate, sodium-n-dodecanoate, and sodium-n-decanoate with a tail having a polymerizable substituent.

3. A process as recited in claim 1, wherein said hydrophilic monomer is selected from the group consisting of 2-hydroxyethyl methacrylate and aqueous acrylamide.

4. A process of making a stabilized polymeric hydrogel material having a matrix containing micropores and a fixed, highly connected network of water-filled macropores, comprising the steps of:
(a) forming a mixture of methylymethacrylate (MMA), azoisobutyronitrile (AIBN), didodecyldimethylammonium bromide (DDAB), and water;
(b) mixing said mixture until it forms a viscous isotropic phase;
(c) equilibrating said phase for at least one week until it forms a cubic phase;
(d) causing said MMA to polymerize in the cubic phase to form a cubic phased body;
(e) locating said body in a water bath;
(e) adding to said water bath a special surfactant which holds DDAB in the water bath and thereby causes the DDAB to diffuse out of the body; and
(f) separating said body from said water bath to obtain said hydrogel material.

5. A process as recited in claim 4, wherein: in step (a)the concentration of the components is the following:
0.26 ml of methylymethacrylate (MMA),
0.004 gm/(ml of mma) of azoisobutyronitrile (AIBN),
1 gm of didodecyldimethylammonium bromide (DDAB), and
1.4 ml of water.

6. A process as recited in claim 4, in which the special surfactant is a nonionic surfactant with a hydrocarbon tail of eight carbon atoms and polar head of four ethylene oxide groups.

7. A process of claim 4 or 1 wherein the hydrogel material from step (f) is used as a cell culture substrate in a process of culturing cells.

* * * * *

UNITED STATES PATENT AND TRADEMARK OFFICE
CERTIFICATE OF CORRECTION

PATENT NO. : 5,244,799
DATED : September 14, 1993
INVENTOR(S) : David Anderson

It is certified that error appears in the above-identified patent and that said Letters Patent is hereby corrected as shown below:

column 9, line 68, "uninterrupted" should read -- interrupted--.

In the claims:

| Col. | Line | |
|------|------|---|
| 10 | 58 | "macropores" should read --micropores--; |
| 11 | 2 | "noniomic" should read --nonionic--; |
| 11 | 13-14 | "dideclytrimethyl" should read -- dodecyltrimethyl--; |
| 11 | 25 | "methylymethacrylate" should read --methylmethacrylate--; |
| 12 | 15 | "methylymethacrylate" should read --methylmethacrylate-- |

Signed and Sealed this

Twenty-second Day of August, 1995

Attest:

BRUCE LEHMAN

*Attesting Officer*    *Commissioner of Patents and Trademarks*